(12) United States Patent
Mikkaichi et al.

(10) Patent No.: US 7,722,631 B2
(45) Date of Patent: May 25, 2010

(54) METHOD FOR SUTURING PERFORATION

(75) Inventors: Takayasu Mikkaichi, Tokyo (JP); Kunihide Kaji, Tokyo (JP)

(73) Assignee: Olympus Medical Systems Corporation, Tokyo (JP)

(*) Notice: Subject to any disclaimer, the term of this patent is extended or adjusted under 35 U.S.C. 154(b) by 822 days.

(21) Appl. No.: 11/238,017

(22) Filed: Sep. 28, 2005

(65) Prior Publication Data

US 2007/0073321 A1   Mar. 29, 2007

(51) Int. Cl.
*A61B 17/04* (2006.01)

(52) U.S. Cl. .................. 606/144; 606/153; 128/898

(58) Field of Classification Search .............. 606/144, 606/139, 153, 167; 600/104, 173; 128/898
See application file for complete search history.

(56) References Cited

U.S. PATENT DOCUMENTS

| | | | |
|---|---|---|---|
| 4,235,238 A | 11/1980 | Ogiu et al. | |
| 4,947,827 A | 8/1990 | Opie et al. | |
| 5,053,041 A | 10/1991 | Asnari et al. | |
| 5,297,536 A | 3/1994 | Wilk | |
| 5,458,131 A | 10/1995 | Wilk | |
| 5,507,754 A | 4/1996 | Green et al. | |
| 5,810,848 A | 9/1998 | Hayhurst | |
| 5,817,108 A | 10/1998 | Poncet | |
| 6,024,747 A | 2/2000 | Kontos | |
| 6,066,146 A | 5/2000 | Carroll et al. | |
| 6,203,554 B1 * | 3/2001 | Roberts ............... | 606/144 |
| 6,352,503 B1 * | 3/2002 | Matsui et al. ............ | 600/104 |
| 6,500,184 B1 * | 12/2002 | Chan et al. ............ | 606/144 |
| 6,535,764 B2 * | 3/2003 | Imran et al. ............ | 607/40 |
| 6,572,626 B1 | 6/2003 | Knodel et al. | |
| 2001/0049497 A1 * | 12/2001 | Kalloo et al. ............ | 604/164.01 |
| 2002/0055757 A1 * | 5/2002 | Torre et al. ............ | 606/192 |
| 2003/0055442 A1 | 3/2003 | Laufer et al. | |
| 2003/0163160 A1 * | 8/2003 | O'Malley et al. ............ | 606/213 |
| 2003/0216613 A1 * | 11/2003 | Suzuki et al. ............ | 600/104 |
| 2003/0236535 A1 | 12/2003 | Onuki et al. | |
| 2004/0249395 A1 | 12/2004 | Mikkaichi et al. | |
| 2005/0059984 A1 | 3/2005 | Chanduszko et al. | |

FOREIGN PATENT DOCUMENTS

| | | |
|---|---|---|
| JP | 10-504222 | 4/1998 |
| JP | 2000-516513 | 12/2000 |
| JP | 2002-233530 | 8/2002 |
| JP | 2004-601 | 1/2004 |
| JP | 2004-358045 | 12/2004 |
| JP | 2005-211690 | 8/2005 |

OTHER PUBLICATIONS

U.S. Office Action dated Nov. 19, 2009.

* cited by examiner

*Primary Examiner*—(Jackie) Tan-Uyen T Ho
*Assistant Examiner*—Jing Ou
(74) *Attorney, Agent, or Firm*—Scully, Scott, Murphy & Presser, P.C.

(57) ABSTRACT

A method for suturing a perforation of the present invention comprises the steps of: inserting an observation device into the hollow organ and confirming a proposed incision line for incising the hollow organ; determining a position to be sutured before incising the hollow organ along the proposed incision line; and suturing the perforation by tightening up a suture thread that penetrates through the hollow organ via the position to be sutured after incising the hollow organ along the proposed incision line and performing a medical treatment in an abdominal cavity through the perforation.

5 Claims, 14 Drawing Sheets

METHOD FOR SUTURING PERFORATION

BACKGROUND OF THE INVENTION

1. Field of the Invention

This invention relates to a transendoscopic suturing method. For example, this invention relates to a method for suturing a perforation formed in a wall of a hollow organ.

2. Description of Related Art

In the case of performing a treatment in a body of a patient, the treatment can be performed by incising the body of the patient by a surgical operation, or by an oral endoscopic treatment or a transanal endoscopic treatment. In the case of using an endoscope, the treatment can be performed by putting through a channel of the endoscope a forceps, high-frequency treatment instrument, incision instrument, or suturing apparatus. In the case of using an endoscope inserted in the lumen from a natural opening of a living body such as, for example, the mouth or anus to perform a medical treatment in the abdominal cavity, tissue is resected from the abdominal cavity or incised to form a hole, through which the medical treatment is carried out by moving the endoscope from the lumen to the abdominal cavity. After the end of the medical treatment, the formed hole is sutured by using a suturing apparatus.

A method for suturing a perforation formed in a hollow organ is disclosed in FIG. 1, FIG. 4, and FIGS. 5A to 5C of U.S. Pat. No. 5,297,536. According to this method, a flexible endoscope is inserted into the vicinity of the perforation via the mouth or the anus. Ambient tissue is aspirated by a tube of the flexible endoscope. An O-ring equipped at the outside of the tube is pushed out from the tip of the tube, and the aspirated tissue is clamped by the O-ring.

According to a suturing method shown in FIGS. 6 to 9 of Japanese Laid-Open Patent Application No. 2004-601, the tissue is drawn into an overtube, and a needle is penetrated from the proximal end to the distal end of this tissue. From the inside of the needle, an anchor with a suture thread is pushed out to the distal end of the tissue. After that, the needle is drawn out, and thereby the suture thread penetrates into the tissue, and tightens up the tissue.

SUMMARY OF THE INVENTION

According to an aspect of the present invention, a method for suturing a perforation of the present invention comprises the steps of: inserting an observation device into the hollow organ and confirming a proposed incision line for incising the hollow organ; determining a position to be sutured before incising the hollow organ along the proposed incision line; and suturing the perforation by tightening up a suture thread that penetrates through the hollow organ via the position to be sutured after incising the hollow organ along the proposed incision line and performing a medical treatment in an abdominal cavity through the perforation.

DETAILED DESCRIPTION OF THE INVENTION

First Embodiment

Figure 1:
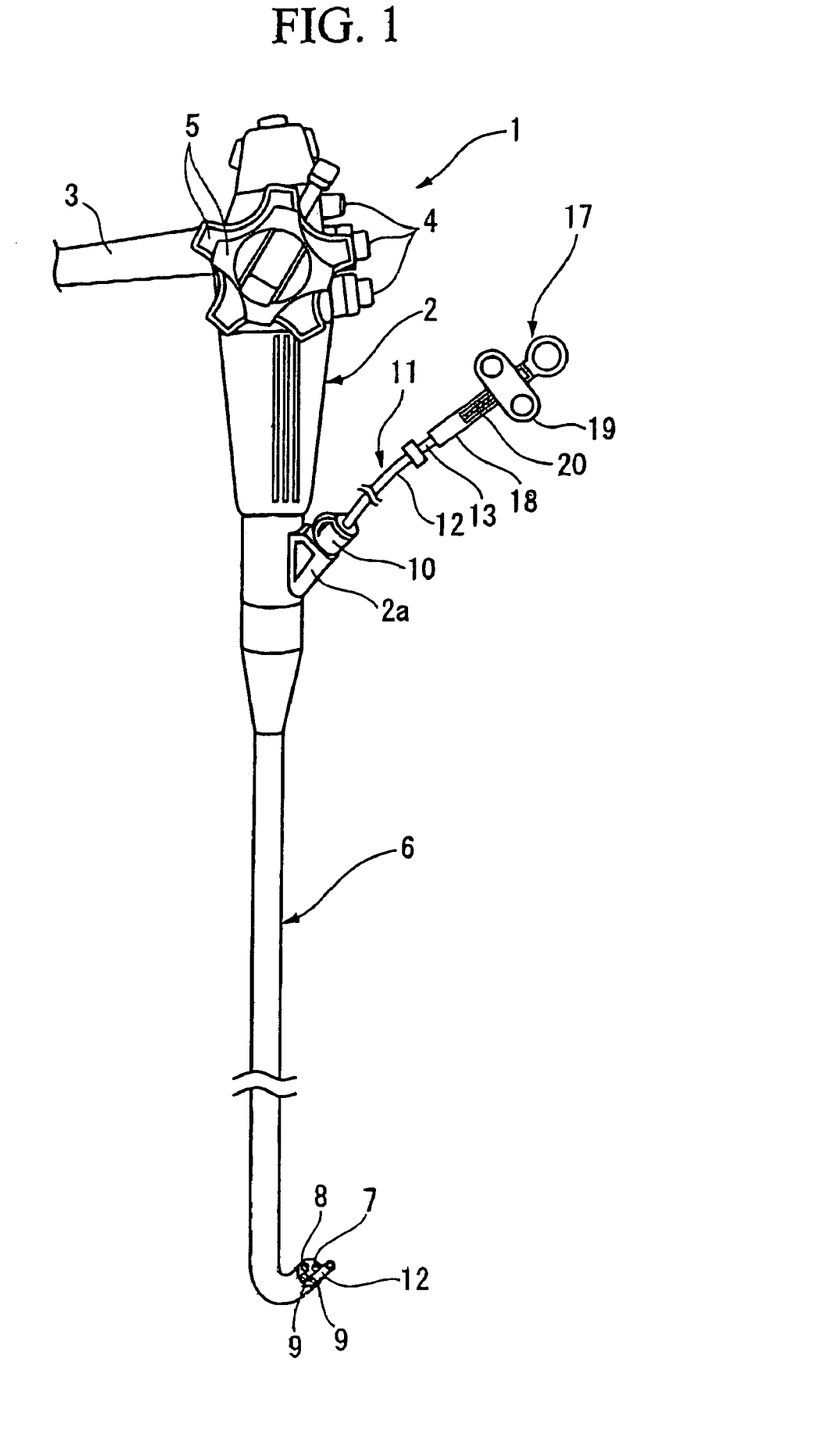
FIG. 1 is a view showing a schematic constitution of an endoscope and a suture instrument.

FIG. 1 shows an endoscope and a suture instrument which are used in this embodiment. An endoscope 1 (flexible endoscope) has an endoscope operation unit 2 which is operated by an operator. The endoscope operation unit 2 is connected to a control device via a universal cable 3 and equipped with various switches 4 and angle knobs 5. At the tip of the endoscope operation unit 2, an endoscope insertion part 6 that is flexible and long is extendedly formed. At the tip of the endoscope insertion part 6, an observation device 7 for obtaining an image of the internal body, a lighting unit 8, and a tip opening of a channel 9 are equipped. As the observation device 7, an imaging device having CCD (Charge Coupled Device) or an optical fiber can be used. The lighting unit 8 has an optical fiber that conducts light from a light source. The channel 9 opens at a lateral part 2a of the endoscope operation unit 2 through the endoscope insertion part 6. A cap 10 is provided at the opening of the lateral part 2a. In the cap 10, an insertion hole is formed, and a treatment instrument such as a suture instrument 11 or the observation device is inserted into the channel 9 through this insertion hole.

Figure 2:
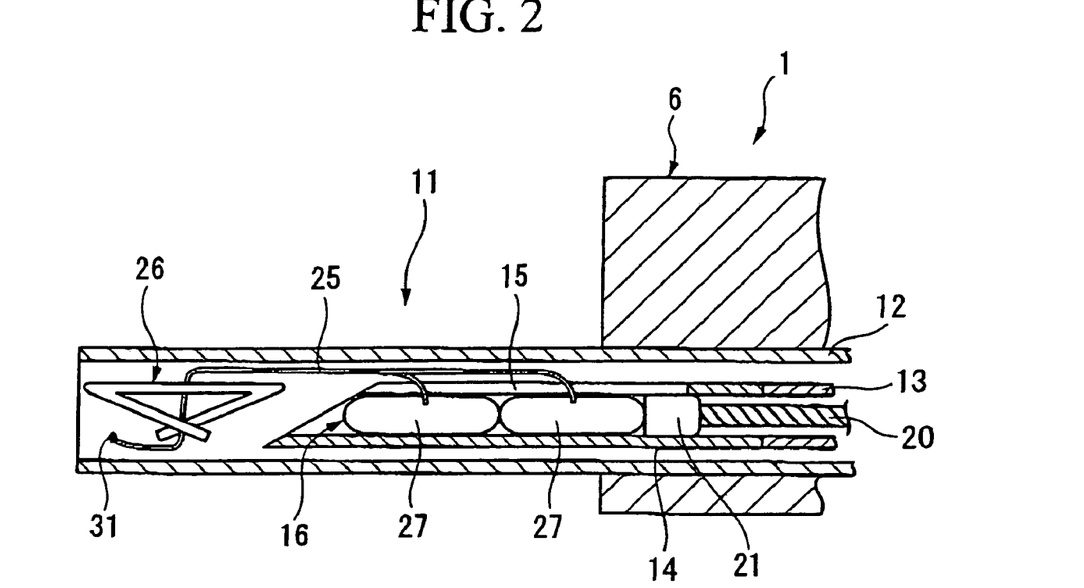
FIG. 2 is a cross-sectional view of a suture instrument and a tip of an endoscope.
Figure 3:
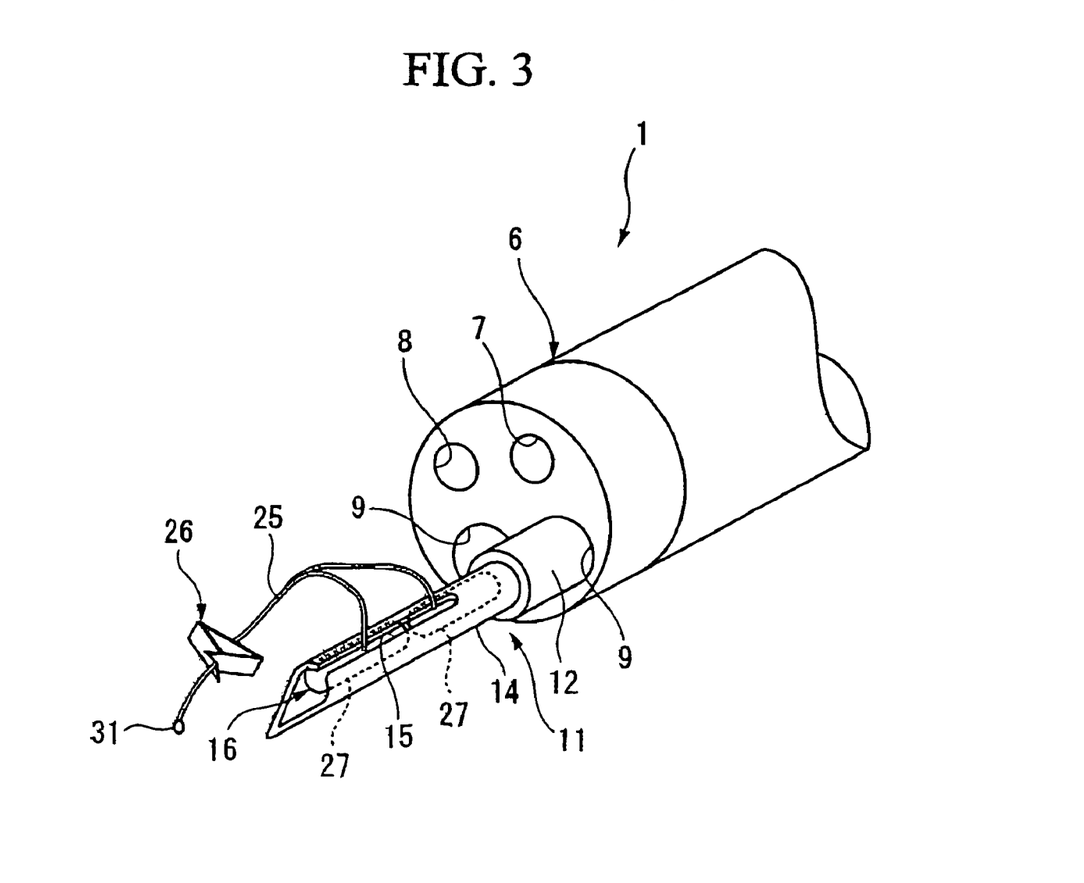
FIG. 3 is a perspective view of a suture instrument and a tip of an endoscope.

As shown in FIGS. 1 to 3, in the suture instrument 11, a flexible inner sheath 13 is passed through the inside of a flexible outer sheath 12 so as to freely move. A needle 14 is fixed to the tip of the inner sheath 13. The needle 14 has a slit 15 formed in a longitudinal direction from the tip thereof. A suture unit 16 is held in the inside of the needle 14. Each length of the outer sheath 12 and the inner sheath 13 is longer than that of the channel 9 of the endoscope 1. At the proximal end of the inner sheath 13, an operation unit 17 is provided. The operation unit 17 has a handle 19 which can freely slide with respect to a main body 18 of the operation unit. To the handle 19, the proximal end of a pusher 20 is fixed. The pusher 20 extends through the inside of the inner sheath 13 to the inside of the needle 14. A distal end portion 21 of the pusher 20 is pressed against the suture unit 16.

Figure 4:
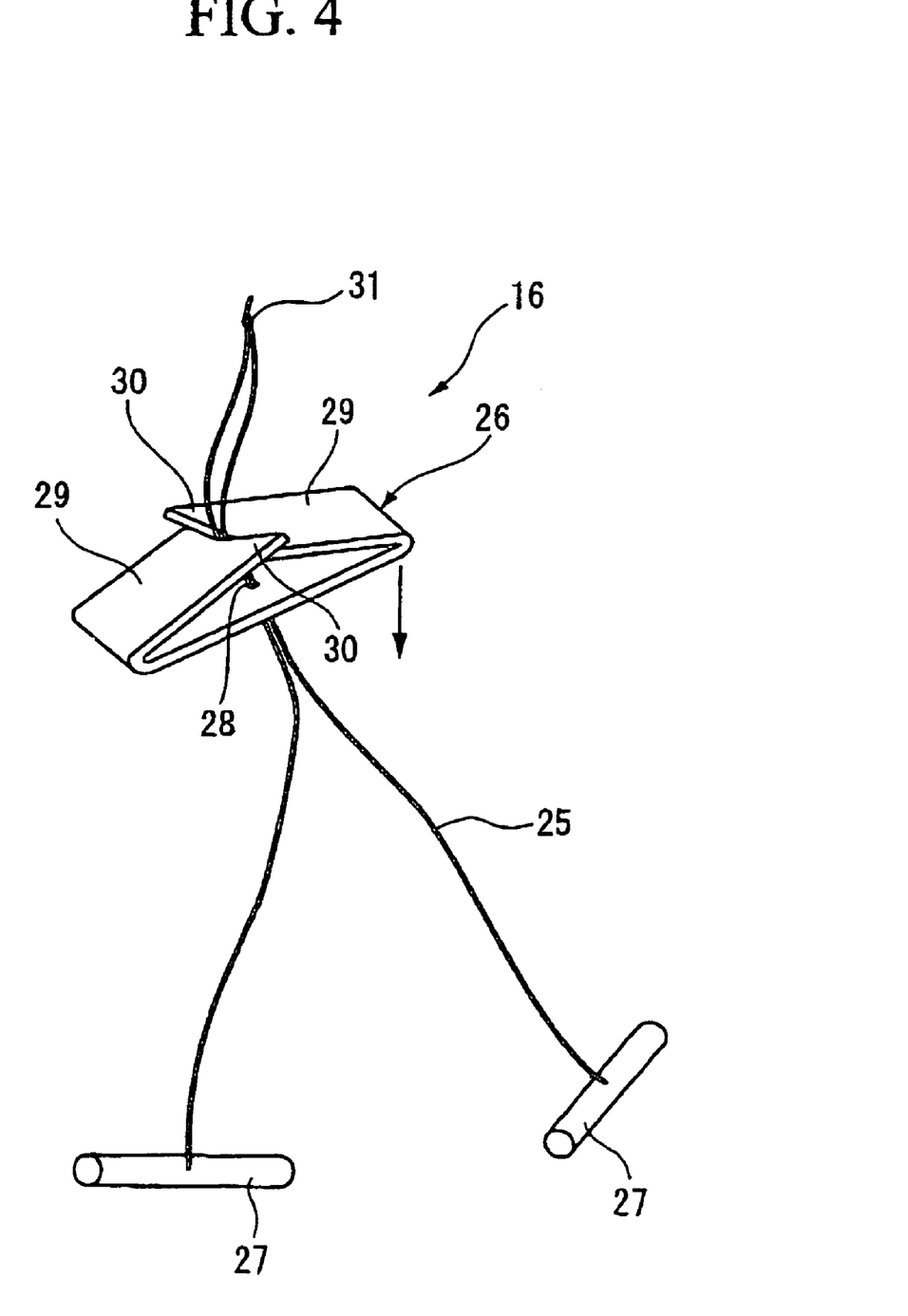
FIG. 4 is a view showing a constitution of a suture unit.

As shown in FIG. 4, the suture unit 16 has a suture thread 25. The suture thread 25 is folded approximately in half and a knot 31 is formed in the vicinity of its turn-around point. Moreover, the suture thread 25 is bundled at both end portions thereof and passed through a stopper 26 that is approximately triangular. To each of both end portions of the suture thread 25, an anchor 27 is fixed. The anchor 27 has a cylindrical shape and the suture thread 25 is fixed to an approximately center portion in a longitudinal direction of the anchor 27. The stopper 26 includes a long, thin plate member having a hole 28 at the center portion in a longitudinal direction thereof, through which the suture thread 25 is passed. Both end portions 29 in a longitudinal direction of the stopper 26 are diagonally folded back to hold the suture thread 25 therebetween. Both of the end portions 29 in a longitudinal direction of the stopper 26 are cut to form triangular sections 30. Both of the end portions 29 of the stopper 26 are diagonally folded back so that the sections 30 are intersected with each other to hold the suture thread 25 therebetween. As a result, the suture thread 25 is prevented from passing through a space formed between the end portions 29. When a knot 31 of the suture thread 25 is pulled in a direction away from the stopper 26, both of the end portions 29 of the stopper 26 are slightly opened. Accordingly, the stopper 26 allows the suture thread 25 to move in the same direction. On the other hand, when end portions of the suture thread 25 at the side of the anchor 27 are pulled, the suture thread 25 is ready to move in a direction shown by an arrow in FIG. 4. At this time, the suture thread 25, however, does not move, since both of the end portions 29 of the stopper 26 are closed and tighten the suture thread 25.

As shown in FIG. 3, the suture unit 16 sequentially holds two anchors 27 in an inner hole of the needle 14. The suture thread 25 is drawn out from the slit 15 of the needle 14. As shown in FIG. 2, the stopper 26 is held at a more distal end portion than the needle 14 in the outer sheath 12. The number of anchors 27 and the shape of the stopper 26 are not limited to the embodiment shown in the figures.

Next, a suturing method of this embodiment will be explained mainly with reference to FIGS. 5 to 16. FIGS. 5 to 16 are pattern diagrams illustrating manipulation and show the stomach as an example of a hollow organ.

Figure 5:
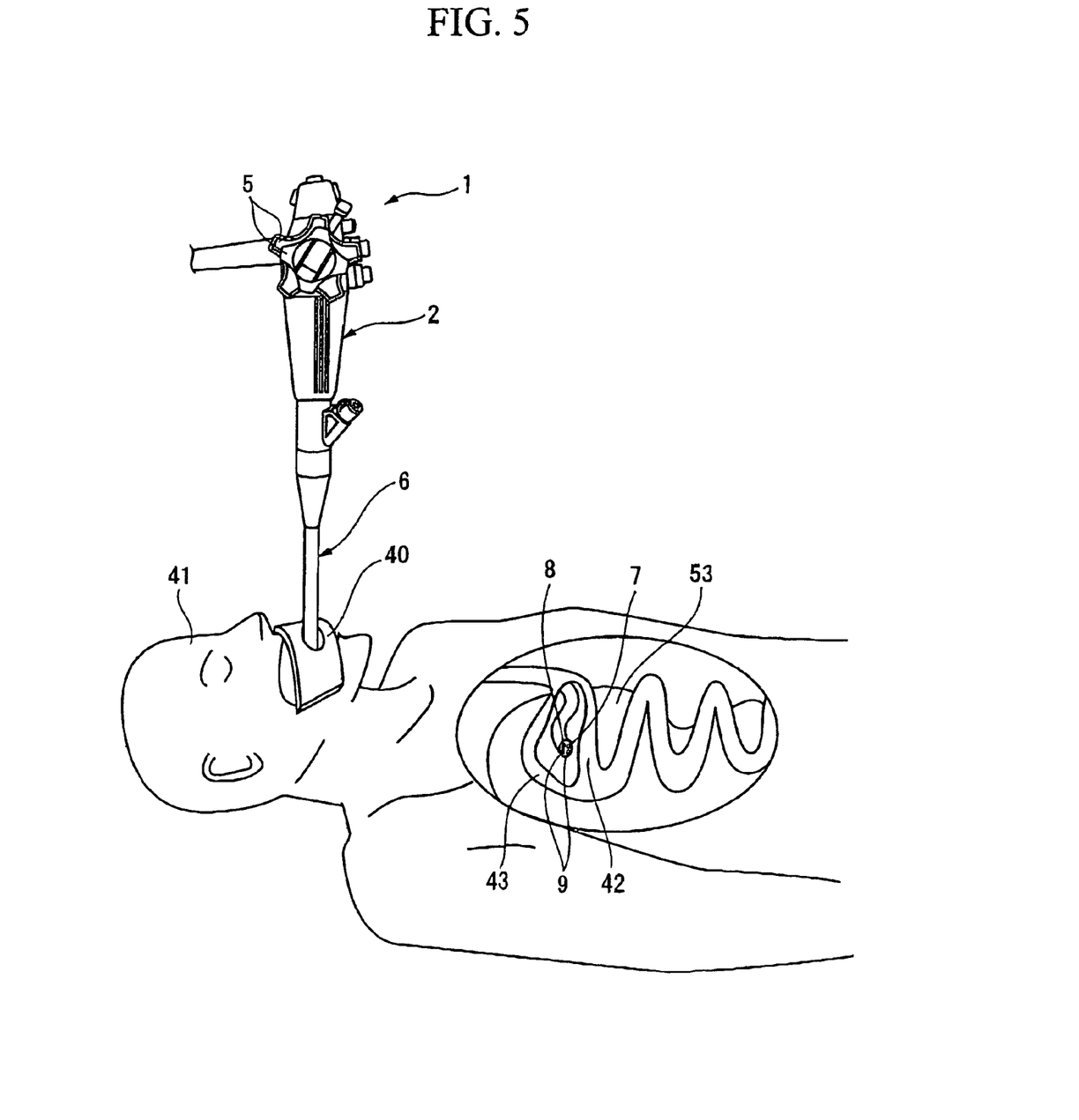
FIG. 5 is a view showing a step of inserting an endoscope into the stomach of a patient to observe a proposed incision position from the inside of the stomach.
Figure 6:
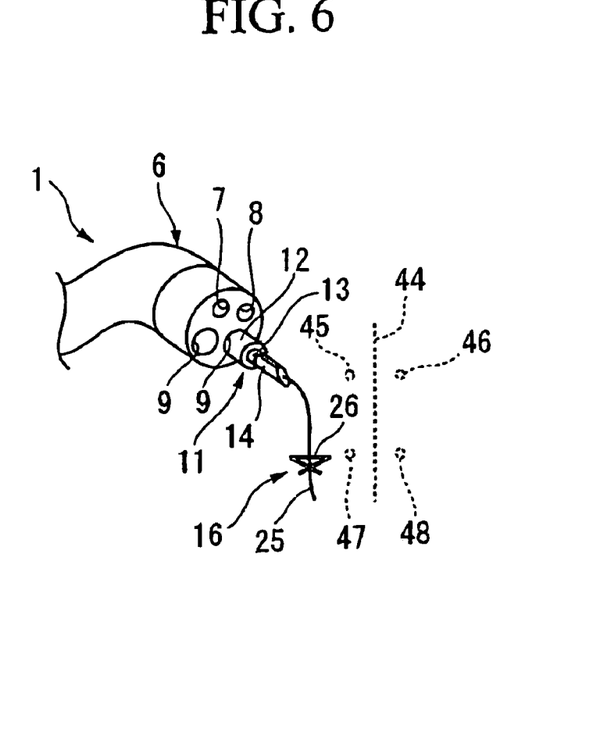
FIG. 6 is a view showing a step of puncturing the position to be sutured with a needle.

As shown in FIG. 5, the endoscope insertion part 6 is inserted from the mouth (a natural opening of a living body, such as the anus, nose, and ear) of a patient 41 equipped with a mouthpiece 40, and the tip of the endoscope insertion part 6 is bent by the angle knob 5. A proposed incision portion 42 shown by a virtual line in FIG. 5 is confirmed from the inside of the stomach 43 (the inside of the hollow organ) by using the observation device 7, and a proposed incision line 44 to be incised thereafter is determined at the proposed incision portion 42. At this time, the proposed incision line 44 may be marked by using a high frequency knife. As shown in FIG. 6, after the suture instrument 11 is projected, the needle 14 is pushed out from the outer sheath 12 so that the stopper 26 is dropped into the stomach 43. The inner sheath 13 of the suture instrument 11 is moved forward, and puncture positions 45, 46, 47, 48 are determined based on the proposed incision line 44 as suture positions to be sutured by the suture instrument 11. The puncture position 45 and the puncture position 46 are mutually symmetrical with reference to the proposed incision line 44, and a line passing through both of the puncture positions 45 and 46 is approximately orthogonal to the proposed incision line 44. The same applies to the puncture positions 47 and 48. At this time, the proposed incision line 44 may be marked by a high frequency knife.

Figure 7:
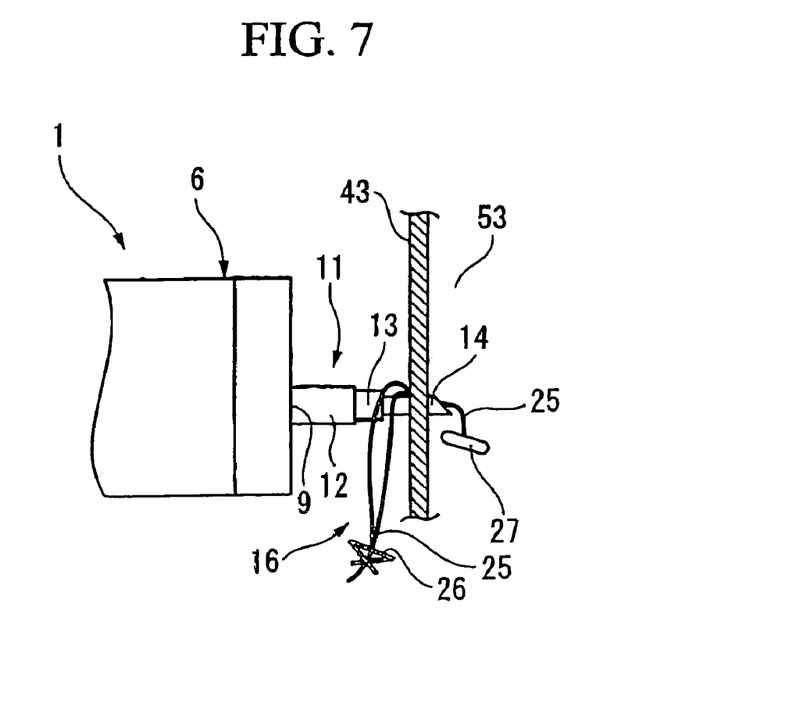
FIG. 7 is a view showing a step of puncturing with a needle and extruding an anchor into the abdominal cavity side.

After determining the puncture positions 45, 46, 47, 48, the first puncture position 45 is punctured with the needle 14. As shown in FIG. 7, after the needle 14 is penetrated through the wall of the stomach 43, the operator-side of the handle 19 is pushed to move the pusher 20 forward. The pusher 20 pushes out the first anchor 27 from the tip of the needle 14 into the outside of the stomach 43 (referred to also as the body cavity side of the hollow organ or the abdominal cavity side). After the first anchor 27 is pushed out, the handle 19 is stopped and the inner sheath 13 is drawn back. The needle 14 is drawn out from the wall, and only the suture thread 25 penetrates through the wall, as a result of which the first anchor 27 is placed at an abdominal cavity 53 side.

Figure 8:
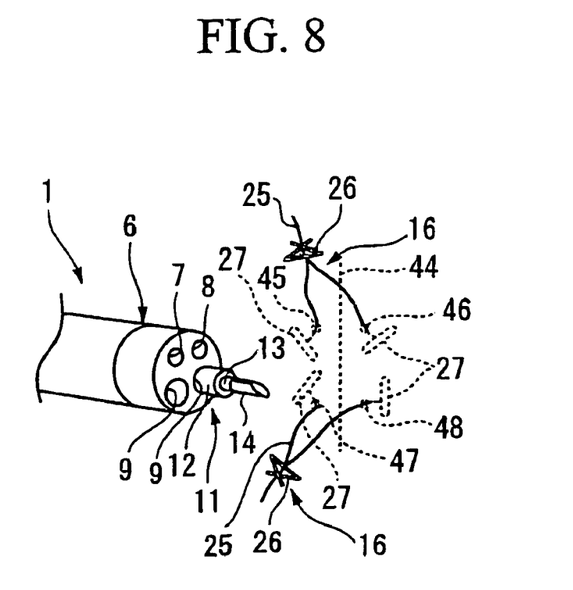
FIG. 8 is a view showing two mounted suture units.
Figure 9:
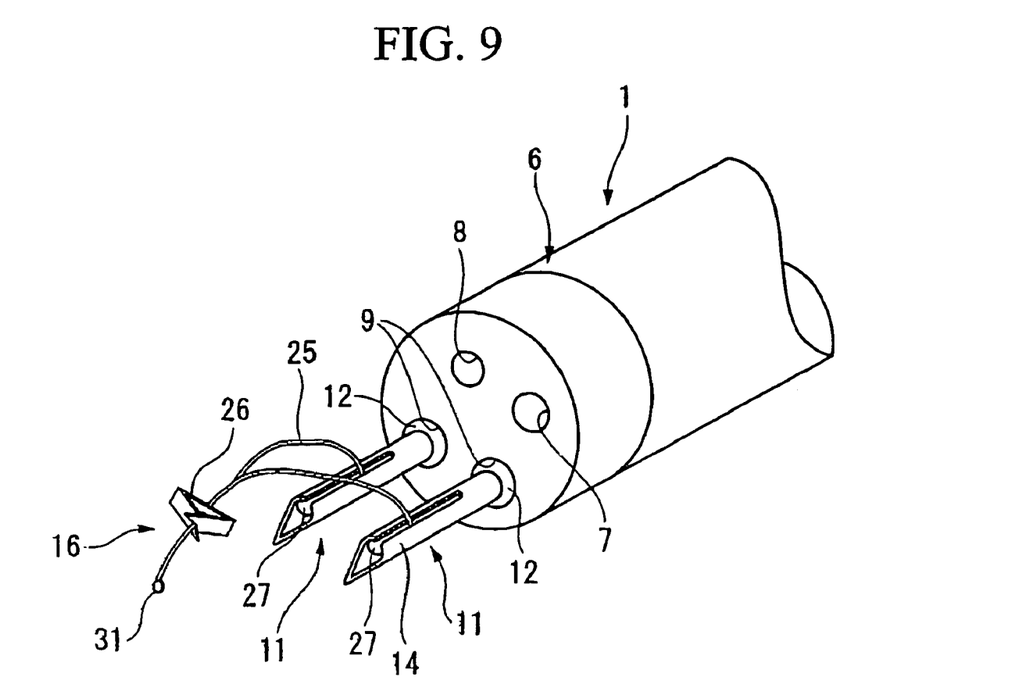
FIG. 9 is a view showing an embodiment in which two suture instruments are respectively passed through two channels.

Next, the needle 14 is punctured at the puncture position 46 that is in a symmetrical position across the proposed incision line 44 as shown in FIG. 6. The second anchor 27 is pushed out into the abdominal cavity 53 in the same way. As shown in FIG. 8, other suture units 16 are mounted on the puncture positions 47 and 48 in the same way. In the case of mounting two suture units 16, the suture instrument 11 may be drawn out from the endoscope 1 after every one of the suture units 16 is mounted, and the suture instrument 11 containing the new suture unit 16 may be passed through the endoscope 1. As shown in FIG. 9, the suture instruments 11 may be respectively passed through two channels 9 in advance, and then the suture units 16 are sequentially mounted.

Figure 10:
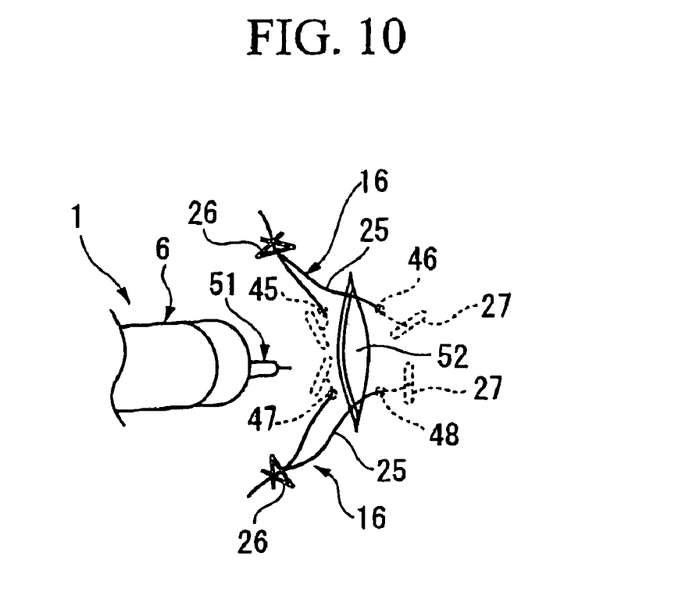
FIG. 10 is a view showing a step of incising a position to be incised.
Figure 11:
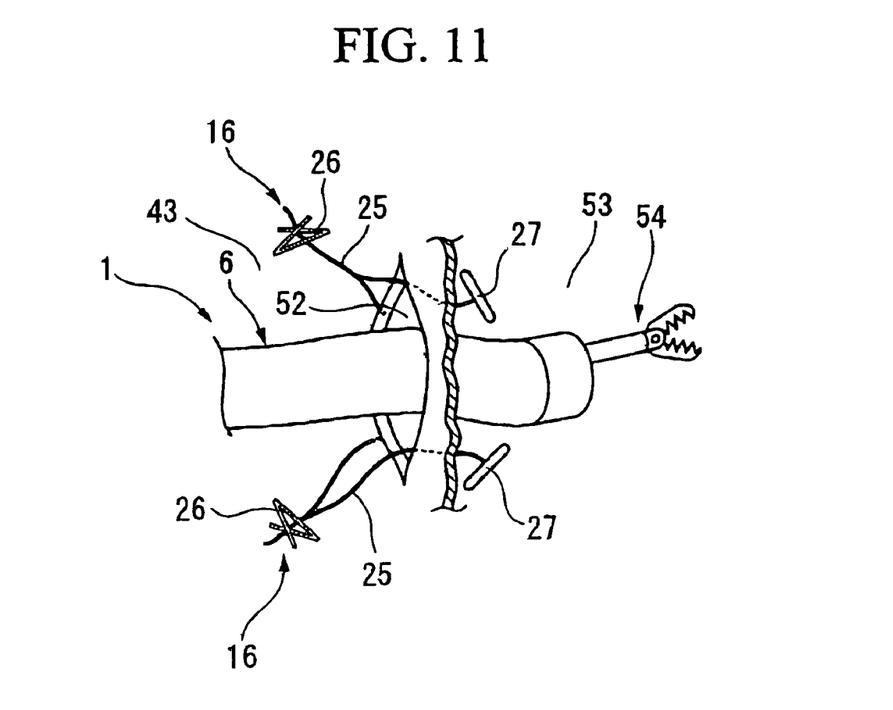
FIG. 11 is a view showing a step of inserting an endoscope insertion part from a perforation into an abdominal cavity for treatment.

After mounting the suture units 16, the proposed incision line 44 is incised. As shown in FIG. 10, an incision instrument such as a needle-like knife 51 which is a high frequency incision tool is passed through the channel 9 of the endoscope insertion part 6. When a high frequency is applied to the tip of the needle-like knife 51, and the needle-like knife 51 is moved along the proposed incision line 44, the wall is incised to form a perforation 52. As shown in FIG. 11, the endoscope insertion part 6 is moved toward the abdominal cavity 53 through the perforation 52. The treatment instrument such as a forceps 54 is passed through the channel 9, and medical treatment is carried out in the abdominal cavity 53.

Figure 12:
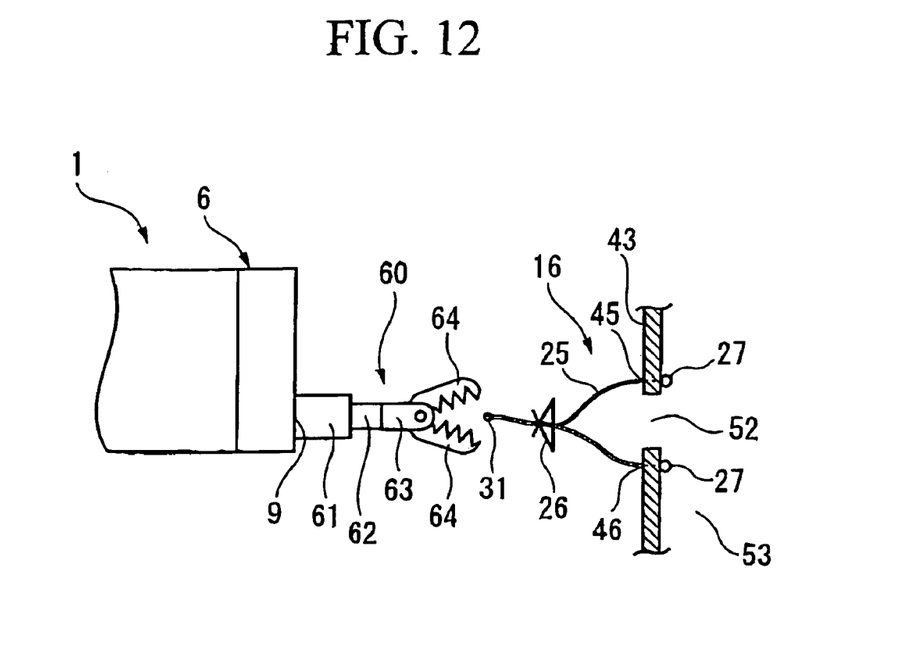
FIG. 12 is a view in which a forceps is passed through an endoscope for tightening up a suture unit.
Figure 13:
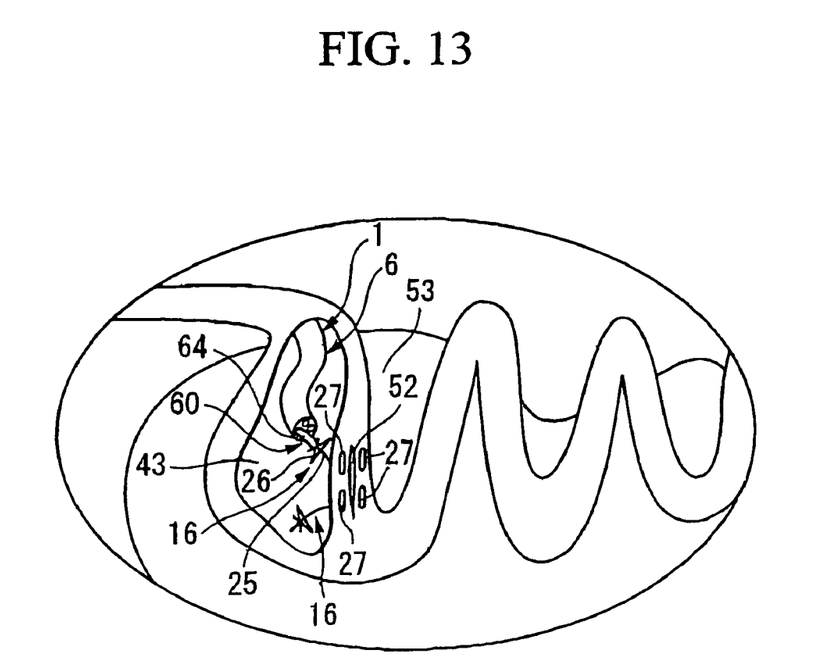
FIG. 13 is a view in which a suture thread of a suture unit is held by a forceps.
Figure 14:
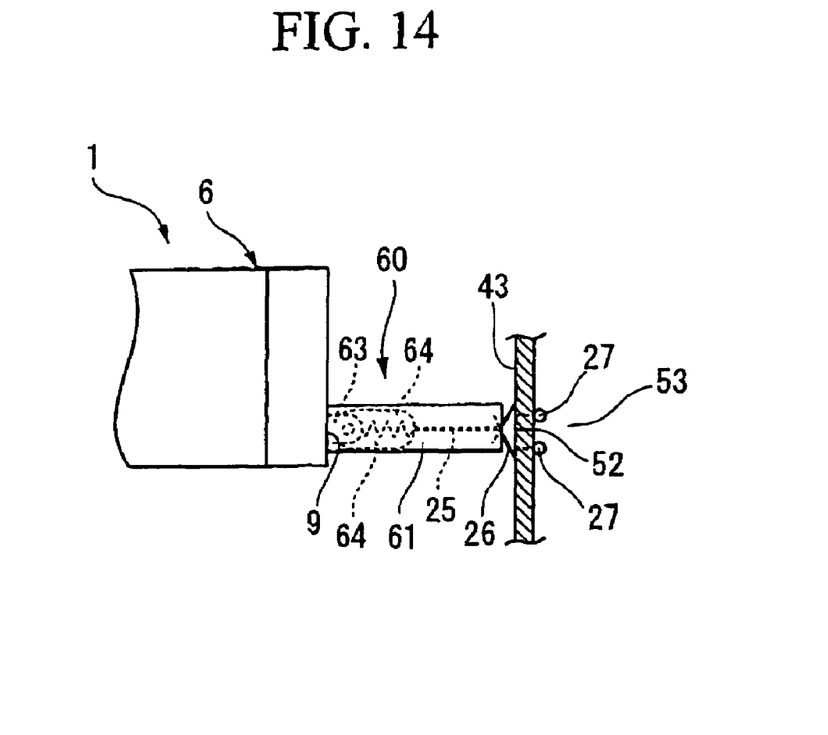
FIG. 14 is a view in which a suture unit is tightened up by an outer sheath of a forceps.

After the end of the medical treatment in the abdominal cavity 53, the endoscope insertion part 6 is drawn back to the inside of the stomach 43, and two suture units 16 are tightened up to suture the perforation 52. In this case, a forceps 60 shown in FIG. 12, for example, is used. The forceps 60 has an outer sheath 61 having a larger external diameter than the anchor 27, and an inner sheath 62 is passed through the outer sheath 61 so as to freely move. A support member 63 is provided at the tip of the inner sheath 62, and a pair of grip segments 64 are supported by the support member 63 so as to freely open and close. As shown in FIG. 13, after the knot 31 of the suture thread 25 of the suture unit 16 is gripped by each of the grip segments 64, the outer sheath 61 is moved forward so that the tip of the outer sheath 61 is pushed against the stopper 26. As shown in FIG. 14, when the outer sheath 61 is moved further forward, the stopper 26 is pushed into the wall of the stomach 43. Since the stopper 26 is formed so as to be capable of moving in this direction, the stopper 26 moves toward the wall. As a result, the distance between the stopper 26 and the anchor 27 is shortened. As a result, the ambient tissue in the perforation 52 is pulled together and the perforation 52 is sutured by the suture thread 25. After the perforation 52 is sutured by using the suture unit 16, the outer sheath 61 is moved backward, followed by opening the grip segments 64 to release the suture thread 25. The tip of the stopper 26 can move in a direction in which the tissue is tightened up by the suture thread 25, and acts in a direction to tighten up the suture thread 25, not in a direction in which the suture thread 25 is loosened. Accordingly, the suture thread 25 does not loosen, even if the suture unit 16 is placed in the stomach 43.

Figure 15:
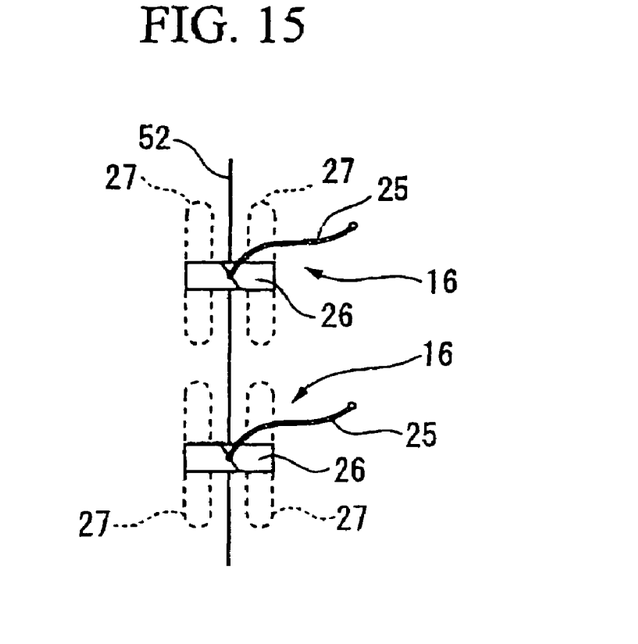
FIG. 15 is a view in which perforations are sutured by tightening two suture units.
Figure 16:
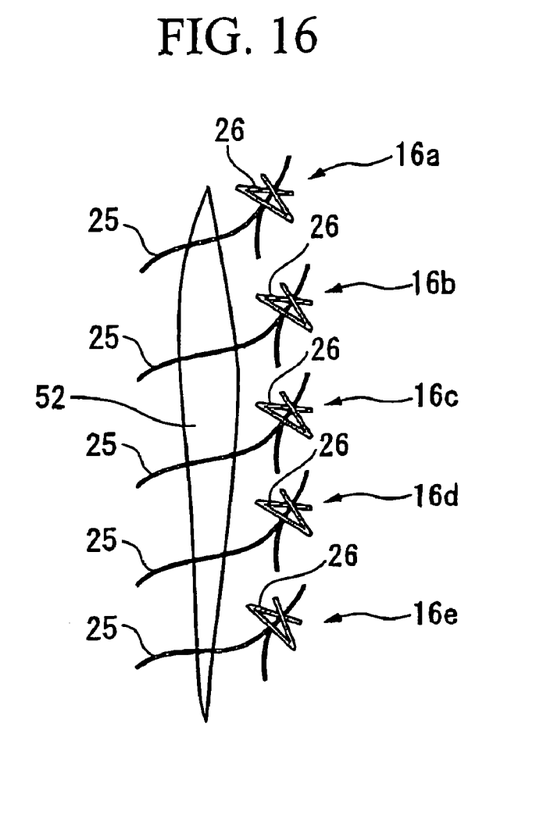
FIG. 16 is a view showing the order in which many suture units are tightened up.

As shown in FIG. 15, the perforation 52 is sutured by sequentially tightening up two suture units 16. In the case of suturing the perforation 52 by using at least three suture units 16 after largely incising the stomach 43, the plural suture units 16 which are lined up may be sequentially tightened up from the ends thereof In an aspect shown in FIG. 16, for example, a suture unit 16a, a suture unit 16b, a suture unit 16c, a suture unit 16d and a suture unit 16e are tightened up in this order. By suturing the perforation 52 from the end thereof, the size of the perforation 52 can be gradually reduced, and thereby suturing becomes easy. Alternatively, one suture unit 16 located in the center of the plural suture units 16 which are lined up may be tightened up at first, and then another suture unit 16 located between the central suture unit 16 which is tightened up and the suture unit 16 located at the end may be tightened up. In the aspect shown in FIG. 16, the suture unit 16c is tightened up at first, the suture unit 16b and the suture unit 16d are then tightened up, and the suture unit 16a and the suture unit 16e are finally tightened up. Since an intermediate position of the opening is sutured every time, displacement between the suture positions is reduced.

According to this aspect, before incising the stomach 43, the displacement between the suture positions can be prevented by mounting the suture units 16 across the proposed incision line 42 in advance. According to the prior art, since a needle is punctured while visually confirming the suture position after incision, the suture positions easily become out of alignment and careful attention is required so as to prevent a leakage from the perforation. In contrast, according to this aspect, since the displacement between the suture positions is prevented, manipulation becomes easy. Moreover, although the field of view is limited and the suture position is required to be determined in view of tissue slipping or elongation since transendoscopic manipulation is restricted to a one-way approach, it becomes possible to reliably close the perforation 52 according to this aspect since the puncture positions 45, 46, 47, and 48 are determined before incision.

Figure 17:
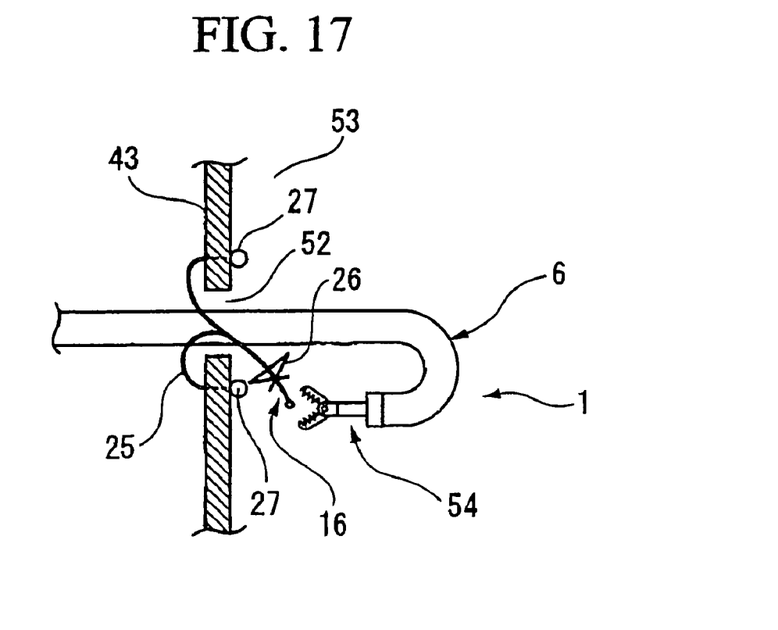
FIG. 17 is a view showing a step of narrowing a perforation in accordance with an endoscope.
Figure 18:
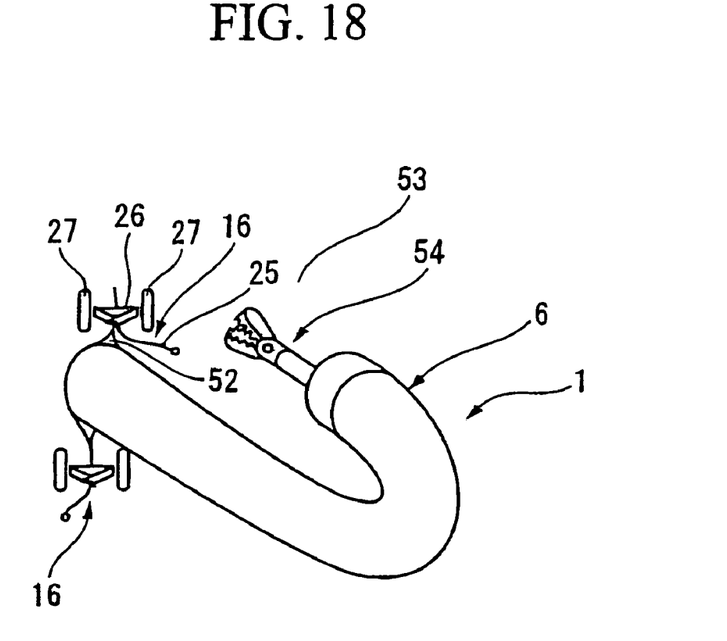
FIG. 18 is a view showing a step of narrowing a perforation in accordance with an endoscope.

At this time, the endoscope insertion part 6 may be moved from the perforation 52 to the abdominal cavity 53 to cut off a large piece of tissue, and then remove it out of the body from the perforation 52 through the stomach 43. When the perforation 52 is formed in accordance with the size of the tissue, the size of the perforation 52 may be larger than the diameter of the endoscope insertion part 6. In this case, when the abdominal cavity is inflated by supplying air from the tip of the endoscope insertion part 6 while carrying out the treatment in the abdominal cavity 53, gas enters the stomach 43 from a gap formed between the endoscope insertion part 6 and the perforation 52. In order to prevent the gas from entering the stomach 43, the suture unit 16 is slightly tightened up to narrow down the size of the perforation 52 to the same size as the endoscope insertion part 6. As shown in FIG. 17, after moving the endoscope insertion part 6 from the perforation 52 into the abdominal cavity 53, the stopper 26 is drawn to the abdominal cavity 53 by the forceps 54 which passes through the endoscope insertion part 6. As shown in FIG. 18, a gap in the perforation 52 is reduced by pushing the stopper 26 to the wall of the stomach 43 by the forceps 54 so as to slightly tighten up the suture unit 16. After that, air is supplied from the tip of the endoscope insertion part 6 to inflate the abdominal cavity 53. After the end of the treatment, the endoscope insertion part 6 is drawn back into the stomach 43. The stopper 26 is drawn into the stomach 43 by using the forceps 54, and the suture unit 16 is tightened up. As a result, the perforation 52 is sutured.

Figure 19:
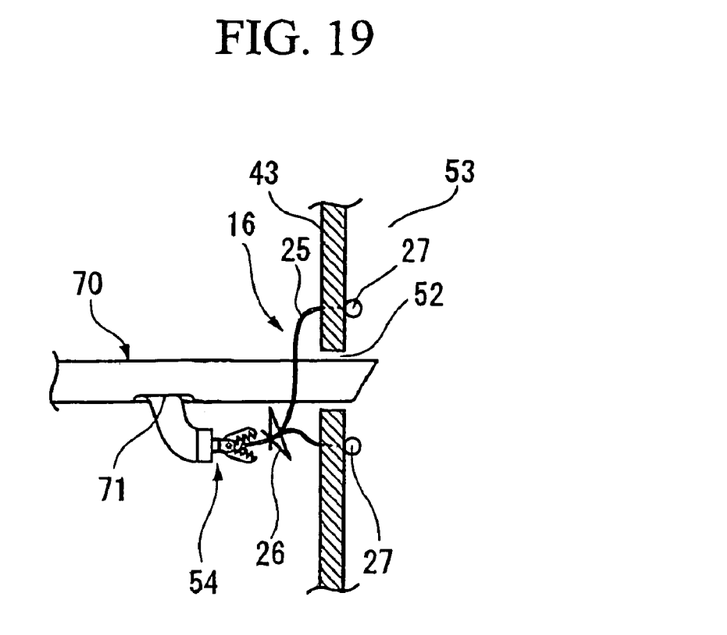
FIG. 19 is a view showing a step of narrowing a perforation in accordance with an overtube.
Figure 20:
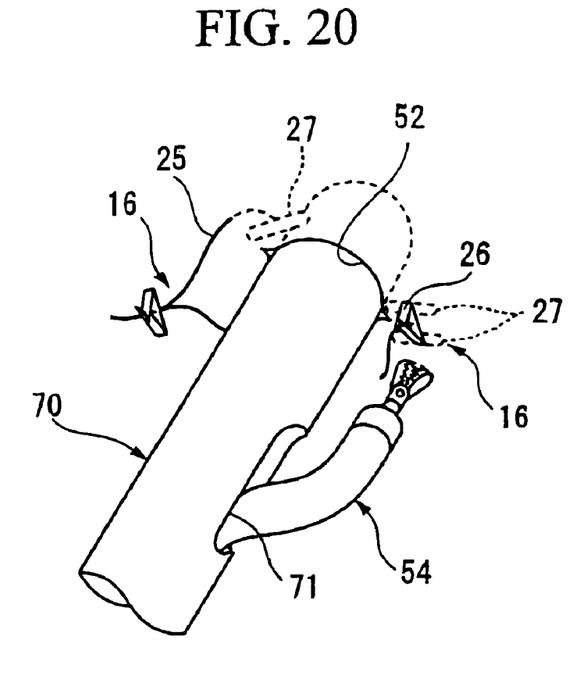
FIG. 20 is a view showing a step of narrowing a perforation in accordance with an overtube.

As shown in FIG. 19, when the endoscope insertion part 6 is passed through an overtube 70 for manipulation, the tip of the overtube 70 is projected from the perforation 52 into the abdominal cavity 53. As shown in FIG. 20, the forceps 54 is introduced from a side hole 71 of the overtube 70 that is inside of the stomach 43, and the suture unit 16 is slightly tightened up to narrow down the size of the perforation 52 to the same size as the external diameter of the overtube 70. The endoscope insertion part 6 is projected from the tip of the overtube 70, and the abdominal cavity 53 is inflated by air for treatment. After the end of the treatment, the overtube 70 is drawn back from the perforation 52. After that, the suture unit 16 is tightened up by using the forceps 54, and thereby the perforation 52 is sutured.

Second Embodiment

In this embodiment, the same endoscope (observation device) 1 and suture instrument 11 as in the first embodiment are used. Descriptions that overlap with the first embodiment will be omitted.

Figure 21:
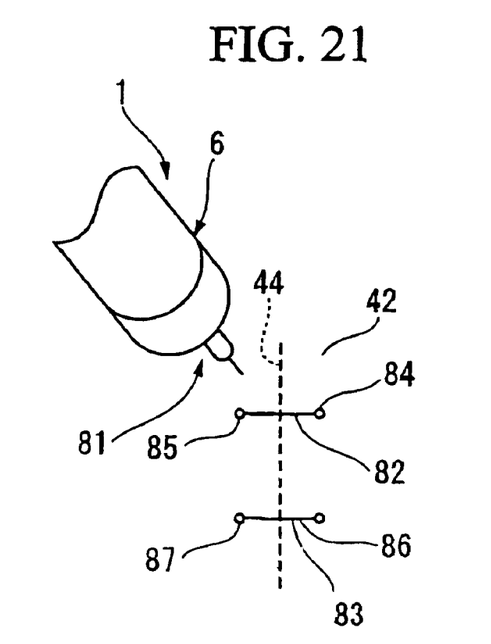
FIG. 21 is a view showing a step of drawing a mark indicating a position to be sutured based on a proposed incision line.

A suturing method of this embodiment will be explained. As shown in FIG. 5, after the endoscope insertion part 6 is inserted from the mouth of the patient 41 with the mouthpiece 40, the tip of the endoscope insertion part 6 is bent by the angle knob 5, and the proposed incision portion 42 is confirmed by the observation device 7. As shown in FIG. 21, a needle-like knife 81 that is a treatment instrument passed through the channel 9 is used to draw a mark 82 that corresponds to the proposed incision line 44 and the suture position. The marks 82 and 83 are line segments that are approximately orthogonal to the proposed incision line 44, and respective approximate middle points of the marks 82 and 83 intersect with the proposed incision line 44. Both end portions 84 and 85 of the mark 82 and both end portions 86 and 87 of the mark 83 respectively correspond to puncture positions. These end portions 84 to 87 may be more largely marked than other portions, or may be marked at the same size as other portions. The marks 82 and 83 may be dots indicating only the puncture positions, circles, or crosses.

Figure 22:
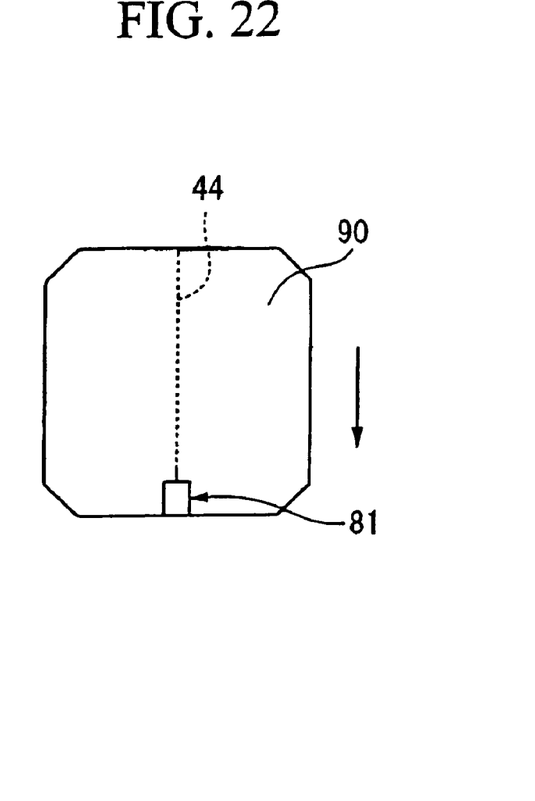
FIG. 22 is a view showing a step of drawing a proposed incision line.

When the proposed incision line 44 is drawn, it is preferable that the tip portion of the needle-like knife 81 is controlled to be on a center line of a field of view 90 of the observation device 7, as shown in FIG. 22. In this alignment, since the proposed incision line 44 can be drawn in the center of the field of view 90, the marks 82 and 83 are easily formed so as to be at accurate positions or to have accurate length. Moreover, when the proposed incision line 44 is drawn, it is preferable that the position of the endoscope insertion part 6 be adjusted in a direction shown by an arrow in FIG. 22 by operating the angle knob 5 of the endoscope 1. In association with the movement of the endoscope insertion part 6, the needle-like knife 81 moves in the same direction. As a result, the proposed incision line 44 can be drawn while constantly confirming the trajectory of the proposed incision line 44. Accordingly, the proposed incision line 44 can be easily and linearly drawn. Moreover, when the needle-like knife 81 is set on the center line of the field of view 90 for drawing each of the marks 82 and 83, it becomes easy to draw the marks 82 and 83 with accuracy.

Figure 23:
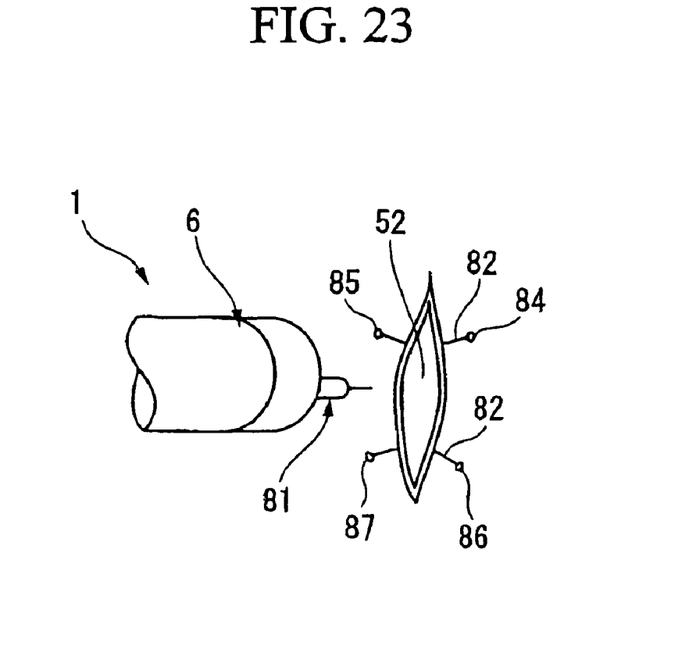
FIG. 23 is a view showing a step of forming a perforation by incising a proposed incision line.
Figure 24:
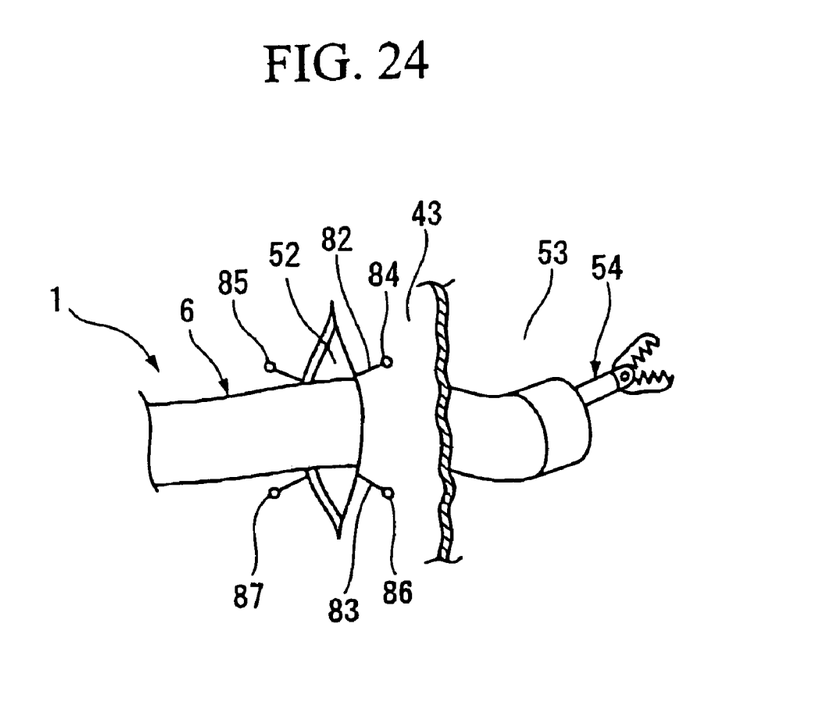
FIG. 24 is a view showing a step of inserting an endoscope insertion part through a perforation into the abdominal cavity for treatment.
Figure 25:
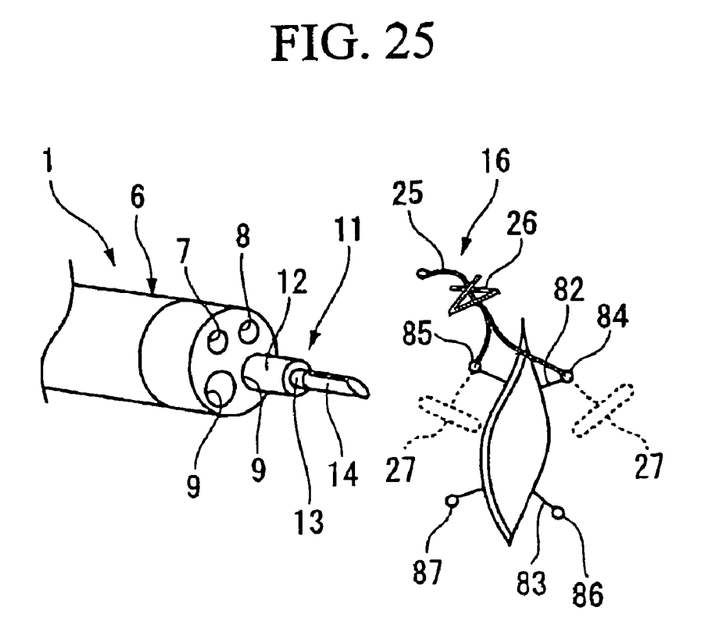
FIG. 25 is a view in which a suture unit is mounted in line with a mark.

After drawing the proposed incision line 44 and the marks 82 and 83, the needle-like knife 81 is drawn along the proposed incision line 44 as shown in FIG. 23, and the wall of the stomach 43 is incised to form the perforation 52. As shown in FIG. 24, the endoscope insertion part 6 is directed through the perforation 52 to the abdominal cavity 53, and the forceps 54 and the like are passed through the channel 9 to carry out the medical treatment in the abdominal cavity 53. After finishing the medical treatment, the endoscope insertion part 6 is drawn back to the stomach 43. Next, two suture units 16 are sequentially mounted to the wall of the stomach 43 by the suture instrument 11. In a manner similar to FIG. 7, one end portion 84 of the mark 82 is punctured with the needle 14 to penetrate the wall. After the pusher 20 is moved forward to extrude the first anchor 27 into the abdominal cavity 53 side, the needle 14 is drawn out. After the other end portion 85 of the mark 82 is punctured with the needle 14, and the second anchor 27 is extruded into the abdominal cavity 53 side, the needle 14 is pulled out. As a result, the first suture unit 16 is mounted on the suture position indicated by the mark 82 as shown in FIG. 25. According to the same procedure, the second suture unit 16 is set on the suture position indicated by the mark 83, and mounted thereon. After that, two suture units 16 are sequentially tightened up by the forceps 60 as shown in FIGS. 12 and 14. As shown in FIG. 15, after the perforation 52 is sutured, the endoscope insertion part 6 is removed from the patient.

In this embodiment, since the marks 82 and 83 indicating the positions to be punctured with the suture unit 16 are made before forming the perforation 52, it is possible to prevent slippage between the suture positions of the perforation 52. Because only marking is carried out in advance and the suture unit 16 is mounted after the end of the treatment, the suture unit 16 does not get in the way during the treatment. Other effects are the same as those of the first embodiment.

Moreover, this invention can be widely applied without being limited to the above-mentioned embodiments.

For example, the endoscope 1 may be inserted from the anus into the colon, which is an example of a hollow organ. In this case, the perforation is formed in the colon and sutured.

The marks 81 and 82 may be diagonally drawn with respect to the proposed incision line 44. Only the marks 81 and 82 may be drawn, and the proposed incision line 44 may be merely confirmed without being drawn.

What is claimed is:

1. A method for suturing a perforation of a stomach, comprising the steps of:
    inserting an observation device into the stomach and drawing a proposed incision line;
    determining a position to be sutured before incising the stomach;
    incising the stomach along the proposed incision line to form the perforation and performing a medical treatment in an abdominal cavity through the perforation;
    suturing the perforation by tightening up a suture thread that penetrates through the stomach via the position to be sutured after performing the medical treatment;
    wherein the step of determining the position to be sutured comprises the step of:
    determining puncture positions which are mutually symmetrical with reference to the proposed incision line by drawing on the stomach a mark on each of the puncture positions and drawing a line connecting the mark on each of the puncture positions, wherein the line is approximately orthogonal to the proposed incision line;
    puncturing the puncture positions with a needle of a suture instrument to make the needle penetrate through a wall of the stomach;
    pushing out anchor from a tip of the needle into an outside of the stomach, the anchor being fixed to the suture thread; and
    drawing out the needle from the wall to make only the suture thread penetrate through the wall and to place the anchors at the outside of the stomach.

2. The method according to claim 1, wherein when performing the medical treatment in the abdominal cavity through the perforation, an endoscope is inserted into the abdominal cavity from a natural opening of a living body through the perforation, and a size of the perforation is narrowed down by using a suture unit in accordance with the size of the endoscope.

3. A method for suturing a perforation of a stomach, comprising the steps of:
    inserting an observation device into the stomach and drawing a proposed incision line;
    determining a position to be sutured before incising the stomach;
    incising the stomach along the proposed incision line to form the perforation and performing a medical treatment in an abdominal cavity through the perforation; and
    suturing the perforation by tightening up a suture thread that penetrates through the stomach via the position to be sutured after performing the medical treatment,
    wherein the step of determining the position to be sutured comprises the steps of:
    determining puncture positions which are mutually symmetrical with reference to the proposed incision line by drawing on the stomach a mark on each of the puncture positions and drawing a line connecting the mark on each of the puncture positions, wherein the line is approximately orthogonal to the proposed incision line, and
    the step of suturing the perforation comprises making the suture thread penetrate the stomach by puncturing the mark with a needle of a suture instrument and placing an anchor fixed to the suture thread at an outside of the stomach.

4. The method according to claim 3, wherein the step of determining the position to be sutured further comprises adjusting a field of view of an observation device so that the proposed incision line is in the center of the field of view of the observation device.

5. The method according to claim 4, wherein the proposed incision line is drawn in the stomach while confirming a trajectory of the proposed incision line is always within the field of view of the observation device.

* * * * *